United States Patent
Takebe

(10) Patent No.: US 7,465,788 B2
(45) Date of Patent: Dec. 16, 2008

(54) BREAST CANCER RESISTANCE PROTEIN (BCRP) AND ANTIBODIES THERETO

(75) Inventor: Naoko Takebe, Elkridge, MD (US)

(73) Assignee: University of Maryland, Baltimore, MD (US)

( * ) Notice: Subject to any disclaimer, the term of this patent is extended or adjusted under 35 U.S.C. 154(b) by 256 days.

(21) Appl. No.: 11/333,542

(22) Filed: Jan. 18, 2006

(65) Prior Publication Data

US 2006/0160139 A1 Jul. 20, 2006

Related U.S. Application Data

(60) Provisional application No. 60/644,706, filed on Jan. 18, 2005.

(51) Int. Cl.
*C07K 14/00* (2006.01)
(52) U.S. Cl. ..................................... 530/350

(58) Field of Classification Search ....................... None
See application file for complete search history.

(56) References Cited

OTHER PUBLICATIONS

Mikayama et al. PNAS, 1993. 90: 10056-10060.*
Burgess et al J Cell Biol. 111:2129-2138, 1990.*
Wang et al. JBC, 2001 276:49213-49220.*
Bowie et al. Science, 247:1306-1310, 1990.*
Metzler et al. Nature Structural Biol. 1997; 4:527-531.*

* cited by examiner

*Primary Examiner*—Michail A Belyavskyi
(74) *Attorney, Agent, or Firm*—Millen, White, Zelano, Branigan, P.C.

(57) ABSTRACT

The present invention provides a breast cancer resistance polynucleotide and protein of *Macaca mulata* (rhesus monkey) and uses thereof. The present invention also provides anti-BCRP antibodies and uses thereof, particularly as a hematopoietic stem cell marker.

11 Claims, 3 Drawing Sheets

FIG 1A

```
BRCP     1-54      MSSSNVEVFIPMSQENTNGFPTTTSNDRKAFTEGAVLSFHNICYRVKVKSGFLP
gi|74136389|ref    MSSSNVEVFIPMSQENTNGFPTTTSNDRKAFTEGAVLSFHNICYRVKVKSGFLP
gi|62526033|ref    MSSSNVEVFIPVSQGNTNGFPATASNDLKAFTEGAVLSFHNICYRVKLKSGFLP
gi|4185796|gb|A    MSSSNVEVFIPVSQGNTNGFPATVSNDLKAFTEGAVLSFHNICYRVKLKSGFLP
gi|27450414|gb|    MSSSNVEVFIPVSQGNTNGFPATASNDLKAFTEGAVLSFHNICYRVKLKSGFLP Cons               ********: ******:*.* ***************:****

BRCP     55-108    GRKPVEKEILSNINGIMKPGLNAILGPTGGGKSSLLDVLAARKDPSGLSGDVLI
gi|74136389|ref    GRKPVEKEILSNINGIMKPGLNAILGPTGGGKSSLLDVLAARKDPSGLSGDVLI
gi|62526033|ref    CRKPVEKEILSNINGIMKPGLNAILGPTGGGKSSLLDVLAARKDPSGLSGDVLI
gi|4185796|gb|A    CRKPVEKEILSNINGIMKPGLNAILGPTGGGKSSLLDVLAARKDPSGLSGDVLI
gi|27450414|gb|    CRKPVEKEILSNINGIMKPGLNAILGPTGGGKSSLLDVLAARKDPSGLSGDVLI Cons                *****************************************************

BRCP     109-162   NGALRPTNFKCNSGYVVQDDVVMGTLTVRENLQFSAALRLPTTMTNHEKNERIN
gi|74136389|ref    NGALRPTNFKCNSGYVVQDDVVMGTLTVRENLQFSAALRLPTTMTNHEKNERIN
gi|62526033|ref    NGAPRPANFKCNSGYVVQDDVVMGTLTVRENLQFSAALRLATTMTNHEKNERIN
gi|4185796|gb|A    NGAPRPANFKCNSGYVVQDDVVMGTLTVRENLQFSAALRLATTMTNHEKNERIN
gi|27450414|gb|    NGAPRPANFKCNSGYVVQDDVVMGTLTVRENLKFSAALRLATTMTNHEKNERIN Cons               * :***********************:**.**********

BRCP     163-216   RVIQELGLDKVADSKVGTQFIRGVSGGERKRTSIGMELITDPSILFLDEPTTGL
gi|74136389|ref    RVIQELGLDKVADSKVGTQFIRGVSGGERKRTSIGMELITDPSILFLDEPTTGL
gi|62526033|ref    RVIQELGLDKVADSKVGTQFIRGVSGGERKRTSIGMELITDPSILFLDEPTTGL
gi|4185796|gb|A    RVIEELGLDKVADSKVGTQFIRGVSGGERKRTSIGMELITDPSILSLDEPTTGL
gi|27450414|gb|    RVIQELGLDKVADSKVGTQFIRGVSGGERKRTSIGMELITDPSILFLDEPTTGL Cons               *:************************************* *****

BRCP     217-270   DSSTANAVLLLLKRMSKQGRTIIFSTHQPRYSIFKLFDSLTLLASGRLMFHGPA
gi|74136389|ref    DSSTANAVLLLLKRMSKQGRTIIFSIHQPRYSIFKLFDSLTLLASGRLMFHGPA
gi|62526033|ref    DSSTANAVLLLLKRMSKQGRTIIFSIHQPRYSIFKLFDSLTLLASGRLMFHGPA
gi|4185796|gb|A    DSSTANAVLLLLKRMSKQGRTIIFSIHQPRYSIFKLFDSLTLLASGRLMFHGPA
gi|27450414|gb|    DSSTANAVLLLLKRMSKQGRTIIFSIHQPRYSIFKLFDSLTLLASGRLMFHGPA Cons               *********************** **************************

BRCP     271-324   QEALGYFESAGYHCEAYNNPADFFLDIINGDSTAVALNREEDFKATEIIEPSKR
gi|74136389|ref    QEALGYFESAGYHCEAYNNPADFFLDIINGDSTAVALNREEDFKATEIIEPSKR
gi|62526033|ref    QEALGYFESAGYHCEAYNNPADFFLDIINGDSTAVALNREEDFKATEIIEPSKQ
gi|4185796|gb|A    QEALGYFESAGYHCEAYNNPADFFLDIINGDSTAVALNREEDFKATEIIEPSKQ
gi|27450414|gb|    QEALGYFESAGYHCEAYNNPADFFLDIINGDSTAVALNREEDFKATEIIEPSKQ Cons                ****************************************************:
```

FIG 1B

```
BRCP      325-378        DKPLVEKLAEIYVDSPFYKETKAELHQLSGGEKKKKITVFKEISYTTSFCHQLR
gi|74136389|ref          DKPLVEKLAEIYVDSSFYKETKAELHQLSGGEKKK-ITVFKEISYTTSFCHQLR
gi|62526033|ref          DKPLIEKLAEIYVNSSFYKETKAELHQLSGGEKKKKITVFKEISYTTSFCHQLR
gi|4185796|gb|A          DKPLIEKLAEIYVNSSFYKETKAELHQLSGGEKKKKITVFKEISYTTSFCHQLR
gi|27450414|gb|          DKPLIEKLAEIYVNSSFYKETKAELHQLSGGEKKKKITVFKEISYTTSFCHQLR Cons                     **:******:*.***************** ***************

BRCP      379-432        WVSKRSFKNLLGNPQASIAQIIVTVILGLVIGGIYFGLNNDSTGIQNRAGVLFF
gi|74136389|ref          WVSKRSFKNLLGNPQASIAQIIVTVILGLVIGAIYFGLNNDSTGIQNRAGVLFF
gi|62526033|ref          WVSKRSFKNLLGNPQASIAQIIVTVVLGLVIGAIYFGLKNDSTGIQNRAGVLFF
gi|4185796|gb|A          WVSKRSFKNLLGNPQASIAQIIVTVVLGLVIGAIYFGLKNDSTGIQNRAGVLFF
gi|27450414|gb|          WVSKRSFKNLLGNPQASIAQIIVTVVLGLVIGAIYFGLKNDSTGIQNRAGVLFF Cons                     ***********************:**.*:************

BRCP      433-486        LTTNQCFSSVSAVELFVVEKKLFIHEYISGYYRVSSYFFGKLLSDLLPMRMLPS
gi|74136389|ref          LTTNQCFSSVSAVELFVVEKKLFIHEYISGYYRVSSYFFGKLLSDLLPMRMLPS
gi|62526033|ref          LTTNQCFSSVSAVELFVVEKKLFIHEYISGYYRVSSYFLGKLLSDLLPMRMLPS
gi|4185796|gb|A          LTTNQCFSSVSAVELFVVEKKLFIHEYISGYYRVSSYFLGKLLSDLLPMRMLPS
gi|27450414|gb|          LTTNQCFSSVSAVELFVVEKKLFIHEYISGYYRVSSYFLGKLLSDLLPMRMLPS Cons                     ***********************************:*************

BRCP      487-540        IIFTCIVYFMLGLKPTADAFFIMMFTLMMVAYSASSMALAIAAGQSVVSVATLL
gi|74136389|ref          IIFTCIVYFMLGLKPTADAFFIMMFTLMMVAYSASSMALAIAAGQSVVSVATLL
gi|62526033|ref          IIFTCIVYFMLGLKPKADAFFVMMFTLMMVAYSASSMALAIAAGQSVVSVATLL
gi|4185796|gb|A          IIFTCIVYFMLGLKPKADAFFVMMFTLMMVAYSASSMALAIAAGQSVVSVATLL
gi|27450414|gb|          IIFTCIVYFMLGLKPKADAFFVMMFTLMMVAYSASSMALAIAAGQSVVSVATLL Cons                     *************.*:******************************

BRCP      541-594        MTICFVFMMIFSGLLVNLTTIASWLSWLQYFSIPRYGFTALQHNEFLGQNFCPG
gi|74136389|ref          MTICFVFMMIFSGLLVNLTTIASWLSWLQYFSIPRYGFTALQHNEFLGQNFCPG
gi|62526033|ref          MTICFVFMMIFSGLLVNLTTIASWLSWLQYFSIPRYGFTALQHNEFLGQNFCPG
gi|4185796|gb|A          MTICFVFMMIFSGLLVNLTTIASWLSWLQYFSIPRYGFTALQHNEFLGQNFCPG
gi|27450414|gb|          MTICFVFMMIFSGLLVNLTTIASWLSWLQYFSIPRYGFTALQHNEFLGQNFCPG Cons                     *****************************************************

BRCP      595-648        LNATVNNTCNYATCTGEEYLTKQGIDLSPWGLWKNHVALACMIVIFLTIAYLKL
gi|74136389|ref          LNATVNNTCNYATCTGEEYLAKQGIDLSPWGLWKNHVALACMIVIFLTIAYLKL
gi|62526033|ref          LNATGNNPCNYATCTGEEYLVKQGIDLSPWGLWKNHVALACMIVIFLTIAYLKL
gi|4185796|gb|A          LNATGNNPCNYATCTGEEYLVKQGIDLSPWGLWKNHVALACMIVIFLTIAYLKL
gi|27450414|gb|          LNATGNNPCNYATCTGEEYLVKQGIDLSPWGLWKNHVALACMIVIFLTIAYLKL Cons                     ** .**********.******************************
```

FIG 1C

```
BRCP      649-655         LFLKKYS
gi|74136389|ref           LFLKKYS
gi|62526033|ref           LFLKKYS
gi|4185796|gb|A           LFLKKYS
gi|27450414|gb|           LFLKKYS Cons                      *******
```

BREAST CANCER RESISTANCE PROTEIN (BCRP) AND ANTIBODIES THERETO

This application claims the benefit of U.S. Provisional Application Ser. No. 60/644,706, filed Jan. 18, 2005, which is hereby incorporated by reference its entirety.

BACKGROUND OF THE INVENTION

Rhesus monkeys (*Macaca mulata*) have been utilized extensively as a pre-clinical model in hematopoietic stem cell transplant research. In order to carry out such research, it is important to be able to identify and isolate the hematopoietic stem cells from rhesus bone marrow or peripheral blood. Recently, BCRP has been focused upon as a marker for the very primitive hematopoietic or other organ stem cells.

Stem cells have the capacity to become at least all differentiated cell types of their lineage in that tissue. Stem cells have two important characteristics that distinguish them from other types of cells. First, they are unspecialized cells that renew themselves for long periods through cell division. Secondly, under suitable conditions they can be induced to become cells with special functions, which may be considered differentiated.

Stem cells have been identified in a variety of tissues. They can be distinguished by a variety of means, such as by the tissue from which they were harvested, their bias in differentiation ability, the stage of development at which they exist, and their gene expression profile. In particular, stem cells may be from ectoderm (epidermal, neural, neural crest, and hair follicle); mesoderm (cardiac muscle, skeletal muscle, umbilical cord blood, mesenchymal, hematopoietic, umbilical cord matrix, and multipotent adult precursor); endoderm (pancreatic islet and hepatic oval); and germ (primordial germ) stem cells. More than one stem cell may be present in a particular tissue. For example, in the hematopoietic system alone, there are stem cells from the yolk sac, fetal cord blood, liver, and adult bone marrow.

Although stem cells may be derived from any tissue harboring stem cells, in particular embodiments they are from bone marrow, embryos, mesenchyme, neural tissue, pancreatic tissue, muscle tissue (such as cardiac muscle), liver, skin, intestine, nasal epithelium, bone, pancreas, or germ cells, for example.

BRIEF DESCRIPTION OF THE DRAWING

FIG. 1 (A-C) shows an amino acid comparison between monkey and human BCRP. BRCP (SEQ ID NO:2); gi|74136389|ref (NP_00102809; *Macaca mulatta;* 654 amino acids; SEQ ID NO:5); gi|62526033|ref (NP_004818; *Homo sapiens;* 655 amino acids; SEQ ID NO:6); gi|4185796|gb|A (AAD09188; *Homo sapiens;* 655 amino acids; SEQ ID NO:7); gi|27450414|gb| (AAO14617; *Homo sapiens;* 655 amino acids; SEQ ID NO:8).

DESCRIPTION OF THE INVENTION

The present invention relates to all facets of rhesus monkey nucleic acids encoding breast cancer resistance protein, including polypeptides encoded by the nucleic acids, antibodies and specific binding partners thereto, and their applications to research, diagnosis, drug discovery, therapy, clinical medicine, forensic science and medicine, etc. The polynucleotides and polypeptides are useful in variety of ways, including, but not limited to, as molecular markers (e.g., for stem cells), as selectable markers (e.g. based on their drug resistance activity), as drug targets, and for detecting, diagnosing, staging, monitoring, prognosticating, preventing or treating, determining resistance to, etc., diseases and conditions.

Breast cancer resistance protein ("BCRP") is an ATP-binding cassette (ABC) transporter gene that is expressed in various tissues, including placenta. It is also known as ATP-binding cassette, subfamily G, member 2 ("ABCG2"). The protein is related to the *Drosophila* white and yeast ADP 1 genes, and is a member of a subfamily that includes several multidrug resistance transporters. Human BCRP was cloned from a multidrug-resistant human breast cancer cell culture line that displayed an ATP-dependent reduction in the intracellular accumulation of anthracycline anticancer drugs. Expression of the full-length BCRP cDNA in MCF-7 human breast cancer cells conferred resistance to mitoxantrone, doxorubicin, and daunorubicin, reduced daunorubicin accumulation and retention, and caused an ATP-dependent enhancement of the efflux or rhodamine-123 in the cloned transfected cells. See, e.g., Doyle et al., *Proc. Nat. Acad. Sci.* 95: 15665-15670, 1998. Thus, polypeptides and polynucleotides of the present invention can be utilized diagnostically to determine the molecular basis for drug diseases and conditions associated with drug resistance, especially cancer in which the resistance has been acquired.

As explained in more detail below, the present invention also provides polynucleotides, polypeptides, and antibodies thereto, which are specific to rhesus monkey BCRP, especially antibodies which are specific and do not cross-react with a human BCRP.

Polynucleotides

A polynucleotide encoding a rhesus monkey (Macaca mulatta) BCRP has been isolated from pancreatic islet cells. The present invention relates to this specific polynucleotide sequence (SEQ ID NO:1;), especially to its coding sequence (from 34-2001 of SEQ ID NO:1), polynucleotides which code for the BRCP polypeptide (SEQ ID NO:2), and derivatives and fragments thereof, including polynucleotides which hybridize to the complement of SEQ ID NO: 1 under high stringency conditions. This includes polynucleotides which code for BCRP and which possess or more activities of BCRP, including, ATPase activity, drug transport activity (e.g., mitoxantrone, topotecan, flavopiridol, and daunorubicin), and ATP-binding activity. Assays for these activities can be carried out routinely. See, e.g., Ozvegy et al., J. Biol. Chem., 277:47980-47990, 2002. For example, the present invention provides a polynucleotide sequence comprising a nucleotide sequence which hybridizes to the complement of SEQ ID NO:1 under high stringency conditions and which codes for a polypeptide having an ATPase and drug transport activity. The coding sequence of such polynucleotide can comprise about 90%, 92%, 96%, 97%, 98%, 99%, or more nucleotide sequence identity along its entire length to the entire length of SEQ ID NO:1. The present invention also provides fragments of such polynucleotides, including fragments having one or more of the above-mentioned activities, including as well the ability to elicit antibodies specific to BCRP. Fragments can comprise, e.g., 20 nucleotide, 40 nucleotides, 50 nucleotides, 57 nucleotides, 60 nucleotides, or more nucleotides, etc.

The present invention also provides polynucleotides comprising, consisting of, consisting essentially of (e.g., having 25 or less, 20 or less, 15 or less, 10 or less, 5 or less, additional polynucleotides at its 5' and/or 3' terminus) a polynucleotide of SEQ ID NO:3, or a polynucleotide coding for SEQ ID NO:4. The present invention also provides polynucleotides which have at least 90%, 95%, 96%, 97%, 98%, 99% or more identity to SEQ ID NO:3, to a polynucleotide coding for SEQ ID NO:4, or to polynucleotides which hybridize to the complement of SEQ ID NO:3 under high stringency conditions. Such polynucleotides can be prepared and/or isolated routinely.

A polynucleotide according to the present invention can be obtained from a variety of different sources. It can be obtained from DNA or RNA, such as polyadenylated mRNA or total RNA, e.g., isolated from tissues, cells, or whole organism. The polynucleotide can be obtained directly from DNA or RNA, from a cDNA library, from a genomic library, etc. The polynucleotide can be obtained from a cell or tissue (e.g., from an embryonic or adult tissues) at a particular stage of development, having a desired genotype, phenotype, disease status, etc. A polynucleotide which "codes without interruption" refers to a polynucleotide having a continuous open reading frame ("ORF") as compared to an ORF which is interrupted by introns or other noncoding sequences, e.g., in the form when isolated from a cDNA library.

A polynucleotide of the present invention can comprise additional polynucleotide sequences, e.g., sequences to enhance expression, detection, uptake, cataloging, tagging, etc. A polynucleotide can include only coding sequence; a coding sequence and additional non-naturally occurring or heterologous coding sequence (e.g., sequences coding for leader, signal, secretory, targeting, tagging, enzymatic, fluorescent, antibiotic resistance, and other functional or diagnostic peptides); coding sequences (e.g., an initiation codon or a leader sequence) and non-coding sequences, e.g., untranslated sequences at either a 5' or 3' end, or dispersed in the coding sequence, e.g., introns.

A polynucleotide according to the present invention also can comprise an expression control sequence operably linked to a polynucleotide as described above. The phrase "expression control sequence" means a polynucleotide sequence that regulates expression of a polypeptide coded for by a polynucleotide to which it is functionally ("operably") linked. Expression can be regulated at the level of the mRNA or polypeptide. Thus, the expression control sequence includes mRNA-related elements and protein-related elements. Such elements include promoters, enhancers (viral or cellular), ribosome binding sequences, transcriptional terminators, etc. An expression control sequence is operably linked to a nucleotide coding sequence when the expression control sequence is positioned in such a manner to effect or achieve expression of the coding sequence. For example, when a promoter is operably linked 5' to a coding sequence, expression of the coding sequence is driven by the promoter. Expression control sequences can include an initiation codon and additional nucleotides to place a partial nucleotide sequence of the present invention in-frame in order to produce a polypeptide (e.g., pET vectors from Promega have been designed to permit a molecule to be inserted into all three reading frames to identify the one that results in polypeptide expression). Expression control sequences can be heterologous or endogenous to the normal gene.

A polynucleotide of the present invention can also comprise nucleic acid vector sequences, e.g., for cloning, expression, amplification, selection, etc. Any effective vector can be used. A vector is, e.g., a polynucleotide molecule which can replicate autonomously in a host cell, e.g., containing an origin of replication. Vectors can be useful to perform manipulations, to propagate, and/or obtain large quantities of the recombinant molecule in a desired host. A skilled worker can select a vector depending on the purpose desired, e.g., to propagate the recombinant molecule in bacteria, yeast, insect, or mammalian cells. The following vectors are provided by way of example. Bacterial: pQE70, pQE60, pQE-9 (Qiagen), pBS, pD10, Phagescript, phiX174, pBK Phagemid, pNH8A, pNH16a, pNH18Z, pNH46A (Stratagene); Bluescript KS+II (Stratagene); ptrc99a, pKK223-3, pKK233-3, pDR540, pRIT5 (Pharmacia). Eukaryotic: PWLNEO, pSV2CAT, pOG44, pXT1, pSG (Stratagene), pSVK3, PBPV, PMSG, pSVL (Pharmacia), pCR2.1/TOPO, pCRII/TOPO, pCR4/TOPO, pTrcHisB, pCMV6-XL4, etc. However, any other vector, e.g., plasmids, viruses, or parts thereof, may be used as long as they are replicable and viable in the desired host. The vector can also comprise sequences which enable it to replicate in the host whose genome is to be modified.

Polynucleotides which hybridize to polynucleotides of the present invention can be selected in various ways. Filter-type blots (i.e., matrices containing polynucleotide, such as nitrocellulose), glass chips, and other matrices and substrates comprising polynucleotides (short or long) of interest, can be incubated in a prehybridization solution (e.g., 6×SSC, 0.5% SDS, 100 μg/ml denatured salmon sperm DNA, 5× Denhardt's solution, and 50% formamide), at 22-68° C., overnight, and then hybridized with a detectable polynucleotide probe under conditions appropriate to achieve the desired stringency. In general, when high homology or sequence identity is desired, a high temperature can be used (e.g., 65° C.). As the homology drops, lower washing temperatures are used. For salt concentrations, the lower the salt concentration, the higher the stringency. The length of the probe is another consideration. Very short probes (e.g., less than 100 base pairs) are washed at lower temperatures, even if the homology is high. With short probes, formamide can be omitted. See, e.g., *Current Protocols in Molecular Biology*, Chapter 6, Screening of Recombinant Libraries; Sambrook et al., *Molecular Cloning*, 1989, Chapter 9.

For instance, high stringency conditions can be achieved by incubating the blot overnight (e.g., at least 12 hours) with a polynucleotide probe in a hybridization solution containing, e.g., about 5×SSC, 0.5% SDS, 100 μg/ml denatured salmon sperm DNA and 50% formamide, at 42° C., or hybridizing at 42° C. in 5×SSPE, 0.5% SDS, and 50% formamide, 100 μg/ml denatured salmon sperm DNA, and washing at 65° C. in 0.1% SSC and 0.1% SDS. Blots can be washed at high stringency conditions that allow, e.g., for less than 5% bp mismatch (e.g., wash twice in 0.1% SSC and 0.1% SDS for 30 min at 65° C.), e.g., selecting sequences having 95% or greater sequence identity.

Polypeptides

The present invention provides polypeptides having an amino acid sequence of SEQ ID NO:2, fragments thereof, and derivatives thereof. An example of a fragment of SEQ ID NO:2 is a polypeptide which consists of NYATCTGEEYLTKQGIDLS (SEQ ID NO:4) which is amino acids 604-622 of SEQ ID NO:2 (e.g., an extracellular region). Also included is Acetyl-NYATCTGEEYLTKQGIDLS-amide (SEQ ID NO:4). Such fragment can be utilized to generate antibodies which are specific to rhesus monkey BCRP, especially a polypeptide of SEQ ID NO:2, and which do not cross-react (i.e., specifically bind to) human BCRP. Such lack of cross-reactivity can be measured when the BCRP polypeptide is expressed in a cell membrane in its normal configuration.

The present invention also provides polypeptides comprising, consisting of, and consisting essentially of (e.g., having 25 or less, 20 or less, 15 or less, 10 or less, 5 or less, etc., additional amino acids at its N- and C-terminus) a polypeptide of SEQ ID NO:4. The present invention also provides polypeptides which have at least 90%, 92% 95%, 96%, 97%, 98%, 99%, etc., or more identity to SEQ ID NO:4. Such polypeptides can be prepared and/or isolated routinely.

The present invention also provides an isolated polypeptide comprising: a) a polypeptide having an amino acid sequence of SEQ ID NO:2, or a polypeptide fragment thereof; or b) a polypeptide which is encoded by a polynucleotide sequence which hybridizes to the complement of SEQ ID NO:1 under high stringency conditions, or a polypeptide fragment thereof, wherein said polypeptide of (a) and (b) is capable of eliciting antibodies which specifically bind to a rhesus monkey BCRP of SEQ ID NO:2.

High stringency conditions can be determined routinely, e.g., to select polynucleotides having at least about 90%, 95%, etc., identity to the complement of SEQ ID NO:2 or SEQ ID NO:4. Specific hybridization conditions are described above. The polypeptides encoded by polynucleotides isolated in such manner are "capable of eliciting antibodies which specifically bind to a rhesus monkey BCRP." By the later phrase, it is meant that, when the polypeptide is used as an immunogen, e.g., in a mouse or rabbit, it produces an immune response that includes antibodies specific to BCRP. Specific binding to BCRP can be determined routinely, e.g., as described below. In addition, antibodies, especially polyclonal antibodies, can be fractionated to separate fractions have a desired specificity, e.g., to a particular region of the polypeptide.

The present invention provides polypeptides which comprise at least one rhesus monkey isoform-specific residue, e.g., selected from the group consisting of: T242, P340, K357, G411, and T615 of SEQ ID NO: 2. The latter nomenclature (e.g., "T242") as used herein indicates the amino acid and residue position at which the amino acid is present (e.g., T242 indicates a threonine is present at amino acid position 242 of SEQ ID NO:2).

The term "monkey isoform-specific residue" refers to the amino acid residues which are specific to the monkey isoform of SEQ ID NO:2, and, e.g., not present in human BCRP of SEQ ID NOS: 6, 7, and 8; and, e.g., not present in rhesus monkey BCRP of SEQ ID NO: 5 which represents a rhesus monkey isoform different from SEQ ID NO:2. FIG. 1 shows an amino acid alignment of rhesus monkey and human BCRP from which these and other position numbers can be determined.

The present invention also provides polypeptides which comprise at least one rhesus monkey-specific residue selected from the group consisting of: M12, T22, R28, V48, G55, P149, V329, D338, I404, G411, N417, F471, T502, I508, V599, and T602. A monkey-specific residue is an amino acid which is specific to a rhesus monkey BCRP (e.g., SEQ ID NO:2), but not present in the human homolog. FIG. 1 shows an amino acid alignment of rhesus monkey and human BCRP from which these and other position numbers can be determined.

The present invention also provides polypeptides which have amino acid substitutions other than those at the indicated position number in FIG. 1, especially at amino acid positions 242, 340, 357, 411, and/or 615 of SEQ ID NO:2; or 12, 22, 28, 48, 55, 149, 329, 338, 404, 411, 417, 471, 502, 508, 599, and/or 602 of SEQ ID NO:2. Conservative and non-conservative amino acid substitutions can be made. Conservative amino acid substitutions include exchanges within one of the following five groups: I. Small aliphatic, nonpolar or slightly polar residues: Ala, Ser, Thr, Pro, Gly; II. Polar, negatively charged residues and their amides: Asp, Asn, Glu, Gln; III. Polar, positively charged residues: His, Arg, Lys; IV. Large, aliphatic, nonpolar residues: Met Leu, Ile, Val, Cys; V. Large, aromatic residues: Phe, Tyr, Trp.

Preferred polypeptides include fragments which contain T615 of SEQ ID NO:2, such as SEQ ID NO:4. Preferred antibodies, or fragment thereof, include antibodies which specifically bind to an epitope present in these polypeptides, especially where the epitope comprises T615.

The polypeptides of the present invention, especially fragments of the polypeptide having an amino acid sequence of SEQ ID NO:2, such as a fragment having the amino acid sequence set forth in SEQ ID NO:4, can also be conjugated or fused to other proteins, such as carrier proteins (e.g., for vaccination purposes) or at its N- or C-terminus for recombinant production, such as for stabilizing the polypeptide or for purification purposes after recombinant expression. Examples of polypeptides that can be fused recombinantly to a polypeptide (e.g., to a polypeptide of SEQ ID NO:4) of the present invention includes, e.g., His, Myc, HA, GST, VSV, beta-gal, lac, GFP, thioredoxin, MBP, and other "tag" sequences which can be used to purify the polypeptide after expression in a host cell. Commercial kits can be used to clone, express (in both eukaryotic and prokaryotic hosts), and purify polypeptides which comprise these polypeptide tags. Expression can be achieved in *E. coli*, yeast, baculovirus, and mammalian systems to produce large amounts of recombinant proteins that may otherwise be difficult to isolate from natural cells and tissues. Antibodies to the fusion proteins (e.g., SEQ ID NO:4 fused to a tag) can be used to monitor protein expression and purification. The peptide tags have their own characteristics which can be employed for purification purposes. Poly-His-fusion proteins (6×His) can bind to Nickel-Sepharose or Nickel-HRP. GST-fusion proteins can bind to glutathione-Sepharose. Therefore, a high degree of purification of fusion protein can be achieved in just one affinity purification step. Fusion proteins can be directly injected into animals to generate antibodies, or the peptide tags can be removed by treatment with enzymes and other cleavage agents to generate tag-free recombinant proteins. The fusion proteins can be produced recombinantly, e.g., by fusing in-frame a polynucleotide coding for the tag sequence to a polynucleotide coding for a BCRP polypeptide (either to its N- or C-terminus).

Amino acid comparisons are shown in FIG. 1 between the BCRP of the present invention and other related BCRP polypeptides. Sequence identity between SEQ ID NO:2 and NP_001028091 (*Macaa mulatta*) is 650/655 (99%); between NP-004818 (human) is 631/655 (96%); between AAD09188 (human) is 629/655 (96%); and between AAO14617 is 630/655 (96%). As indicated above, the isoform of SEQ ID NO:2 contains certain unique amino acid substitutions in comparison to other known forms, and the present invention provides polypeptides which comprise one or more of the following amino acid residues, e.g., T242, P340, G411, and/or T615.

Binding Partners

The polynucleotides and amino acid sequences provided herein are useful for generating antibodies, and other binding partners, against the cell surface membrane polypeptide BCRP (SEQ ID NO:2) in rhesus and other monkeys. Rhesus has been used as a model for hematopoietic stem cell transplantation, and expression of BCRP is known to serve as a marker for primitive hematopoietic stem cells. Therefore, the antibody compositions of the present invention can be used for the detection of BCRP expression in hematopoietic stem cells. A polypeptide comprising SEQ ID NO:4 can be utilized to produce antibodies which are specific to a rhesus BCRP of the present invention. The antibodies can be selected such that they specifically recognize (bind) rhesus BCRP, but not a human BCRP, especially when the polypeptide is displayed on the cell surface or on a cell membrane. Such an antibody can recognize an epitope that comprises, e.g., at least one of T242, P340, K357, G411, and/or T615, especially T615, of SEQ ID NO:2. An antibody can also recognize an epitope comprising at least one of M12, T22, R28, V48, G55, P149, V329, D338, I404, G411, N417, F471, T502, I508, V599, and T602 of SEQ IS NO:2.

Binding partners include, e.g., antibodies, aptamers, and other binding ligands. Antibodies can be of any type, including, e.g., polyclonal, monoclonal, recombinant, chimeric, humanized, single-chain, Fab, and fragments thereof. These can be prepared routinely according to any desired method. See, also, screening recombinant immunoglobulin libraries (e.g., Orlandi et al., Proc. Natl. Acad. Sci., 86:3833-3837, 1989; Huse et al., Science, 256:1275-1281, 1989); in vitro stimulation of lymphocyte populations; Winter and Milstein, Nature, 349: 293-299, 1991. See, also, U.S. Pat. No. 5,260,203 for methods of making and producing single-chain antibodies (e.g., "ScFv") The antibodies can be IgM, IgG, subtypes, IgG2a, IgG1, etc. An antibody specific for a polypeptide (e.g., a polypeptide having the amino acid sequence set forth in SEQ ID NO:4) means that the antibody recognizes and binds to a defined sequence of amino acids within or including the polypeptide.

The term "antibody" as used herein includes intact molecules as well as fragments thereof, such as Fab, F(ab')2, Fv, and single chain antibodies, which are capable of binding to an epitopic determinant present in a BCRP polypeptide. Such antibody fragments retain the ability to specifically bind to a BCRP epitope. The term "epitope" refers to an antigenic determinant on an antigen to which the paratope of an antibody binds. Epitopic determinants usually consist of chemically active surface groupings of molecules such as amino acids or sugar side chains and usually have specific three-dimensional structural characteristics, as well as specific charge characteristics. Antibodies can be prepared against specific epitopes or polypeptide domains.

Various modifications can be made to the polypeptides and antibodies of the present invention, such as attaching detectable markers (e.g., avidin, biotin, enzymes, radioactive elements, fluorescent tags and dyes, energy transfer labels, energy-emitting labels, binding partners, etc.) or moieties which improve detection, and/or stability (e.g., PEG). Examples of fluorescent dyes include, but are not limited to, Alexa Fluor 35, 488, 532, 546, 555, 568, 594, 647, 660, and 680; Fluorescein (FITC); SpectrumGreen; Rhodamine 6G; tetramethylrhodamine (TRITC); SpectrumOrange; Lissamine rhodamine B dye; Texas Red dye, SpectrumRed, PE; APC; Cy5; Cy5.5; Cy7; quantum dots; fluorescent microspheres (see e.g., U.S. Pat. No. 5,786,219), including spheres with magnetic properties (e.g., U.S. Pat. Application No. 20010046602); etc. Examples of enzymes include, e.g., peroxidases and others as mentioned below.

Polyclonal antibodies to the polypeptides can generally be raised in animals by multiple subcutaneous (sc) or intraperitoneal (ip) injections of the polypeptide and an adjuvant. It may be useful to conjugate the polypeptide to a carrier, especially a carrier which is immunogenic in the species to be immunized, e.g., keyhole limpet hemocyanin, serum albumin, bovine thyroglobulin, soybean trypsin inhibitor, or tetanus toxoid. Conjugation can be carried routinely, e.g., using a bifunctional or derivatizing agent, such as maleimidobenzoyl sulfosuccinimide ester (conjugation through cysteine residues), N-hydroxysuccinimide (through lysine residues), glutaraldehyde, succinic anhydride, etc.

The route and schedule for immunization of the host animal are generally in keeping with established and conventional techniques for antibody stimulation and production. Any mammalian subject can be used to generate antibodies, including rabbits, mice, rats, guinea pigs, sheep, goats, and antibody-producing cells obtained from them. Animals can be immunized routinely, e.g., using immunogenic conjugates, or derivatives thereof, by combining 1 mg or 1 µg of conjugate (for rabbits or mice, respectively) with 3 volumes of Freund's complete adjuvant and injecting the solution intradermally at multiple sites. One month later, the animals can be boosted with about 1/20 (or less) to 1/10 the original amount of conjugate in Freund's complete adjuvant (or other suitable adjuvant) by subcutaneous injection at multiple sites. 7 to 14 days later animals can be bled and the serum can be assayed for antibody titer. Animals can be boosted until the titer plateaus.

After immunization, monoclonal antibodies can be prepared by recovering immune lymphoid cells, such as spleen cells or lymphocytes from lymph node tissue, from immunized animals and immortalizing the cells in a conventional fashion, e.g., by fusion with myeloma cells or by Epstein-Barr (EB)-virus transformation and screening for clones expressing the desired antibody. The hybridoma technique described originally by Kohler and Milstein, *Eur. J. Immunol.* 6:511 (1976) has been widely applied to produce hybrid cell lines that secrete high levels of monoclonal antibodies against many specific antigens. It is possible to fuse cells of one species with another. However, typically the source of the immunized antibody producing cells and the myeloma are from the same species.

The hybrid cell lines can be maintained in culture in vitro in cell culture media. The cell lines of this invention can be selected and/or maintained in a composition comprising the continuous cell line in hypoxanthine-aminopterin thymidine (HAT) medium. Hybridoma cell lines can be stored and preserved in any number of conventional ways, including freezing and storage under liquid nitrogen. Frozen cell lines can be revived and cultured indefinitely with resumed synthesis and secretion of monoclonal antibody. The secreted antibody can be recovered from tissue culture supernatant by conventional methods, including precipitation, ion exchange chromatography, affinity chromatography, etc. The antibodies described herein can also be recovered from hybridoma cell cultures by conventional methods for purification of IgG or IgM as the case may be that heretofore have been used to purify these immunoglobulins from pooled plasma, e.g., ethanol or polyethylene glycol precipitation procedures.

Antibodies, and immune responses, can also be generated by administering naked DNA See, e.g., U.S. Pat. Nos. 5,703,055; 5,589,466; and 5,580,859.

Antibodies in accordance with the present invention can also be prepared by recombinant techniques. These include methods for creating recombinant DNA versions of the antigen-binding regions of antibody molecules (known as Fab or variable regions fragments) which bypass the generation of monoclonal antibodies. For example, antibody genes from source cells (including naïve cells and cells expressing the antibody of interest) can be cloned into an appropriate vector and utilized to achieve expression of adequate amounts of functional antibody. Additional techniques can be utilized to select the desired antibody when a large repertoire of genes has been cloned. Recombinant antibodies can be cloned from any species of antibody-producing animal using the appropriate oligonucleotide primers.

The ability to clone antibody genes makes it possible to generate new antibodies in vitro which have increased binding specificity for the target polypeptide, e.g., using affinity maturation techniques. This can be done in various ways, including at the level of the whole combining site by making new combinations of H and L chains (Collet et al., 1992; Kang et al., 1991a; Marks et al., 1992). It can also be done by mutating individual CDRs (Cheetham, 1988; Garrard and Henner, 1993; Kettleborough et al., 1991).

The host in which most recombinant antibody methods were originally developed is the bacterium *Escherichia coli* and other bacterial hosts. Growth of bacteria is rapid and inexpensive, and a number of vectors are available for expression and manipulation of cloned genes. DNA can be introduced directly into *E. coli* (the process known as transformation) or by infectious bacteriophage (transfection). Genetic constructions of antibody fragments (Fab and ScFv) can be quickly assessed and various selection methods can be applied.

Phage selection methods can also be used to prepare recombinant antibodies of the present invention. Phage displaying the desired antibodies can be selected by binding to antigen in a format similar to solid-phase immunoassay (Barbas and Lerner, 1991). The process is generally called "phage panning." The antigen or hapten conjugate is immobilized on microplate wells or on magnetic beads or solid material packed into a column. Bound phage can be eluted and amplified by replication in new host cells. Those that bind weakly or not at all are washed away before the elution step. After several rounds of binding and amplification, the phage population should consist almost entirely of those that express the desired antibodies.

Antibody engineering, the process of altering antibody structure and functional properties by recombinant DNA methods, can also be applied to the antibodies of the present invention. Once the DNA sequences of the variable regions are known, the amino acid sequence can be deduced. Methods of in vitro mutagenesis can be applied to insert, delete, or change one or several amino acids, or to exchange entire variable domains. The structures of many antibodies have been determined by X-ray crystallography at atomic resolution, and the coordinates are stored as files in the Brookhaven Protein Data Bank. These files may be retrieved through the Internet and displayed in many programs available on minicomputers and modeling workstations. Because there is considerable homology among antibody framework domains and the secondary structures of some CDRs, it is possible to construct a computational model of a new antibody in order to predict which CDRs and other residues are important to epitope binding. The model can then be used to guide subsequent engineering and mutagenesis steps (Roberts et al., 1994). The software package AbM (Oxford Molecular, Ltd.) uses established crystallographic structures to build antibody models from amino acid sequence data. The resulting model, which consists of a set of atomic coordinates in three-dimensional space, can be compared to known antibody structures. The mutations can then be introduced into the antibody sequences in the cloning vector, expressed, and assayed routinely for binding affinity and characteristics.

Affinity and specificity, or both, can be modified and improved by changing the relative orientations of VH and VL domains at their interface, lengthening or shortening particular CDRs to enlarge or shrink the binding pocket, increasing the flexibility of CDRs in the combining site, removing or re-spacing some of the side chains that form the combining site, or altering residues that do not contact antigen but help to form the combining site through CDR-CDR and CDR-framework interactions (Roberts et al., 1987). The structure can be changed to accommodate water molecules, metal atoms, and other functional groups. In principle other properties of the antibody-antigen interactions can be changed by altering close-contact residues. The antibody can also be fused with other antibody molecules, toxins, or enzymes.

Synthetic combinatorial antibody libraries have been developed as an alternative to the use of animals for antibody production (Barbas et al., 1992; Hoogenboom and Winter, 1992; Lerner et al., 1992). Based on the knowledge that antigen binding is due primarily to interactions with the six CDR loops in the combining site, antibody diversity can be generated in vitro by limited mutagenesis of one or more CDRs. Such a library can be orders of magnitude more diverse than the $10^5$ to $10^6$ antibodies expressed by the mammalian genome. A library can be displayed on the surface of phage and new antibodies selected by panning as described previously.

Combinatorial library design is based on the unique structural similarities in all antibodies, irrespective of their binding specificity. CDRH3 has the greatest flexibility and conformational variability, and may have the greatest influence on antigen binding. One of the first combinatorial Fab libraries was constructed by making sequence and length variations in CDRH3 of a human Fab specific for tetanus toxoid (Barbas et al., 1992). It is also known that amino acid side chains on at least five of the six CDRs generally contact the epitope (Roberts et al., 1993; Wilson and Stanfield, 1993). Consequently other combinatorial libraries have been constructed by introducing diversity in several of the CDRs (Garrard and Henner, 1993). Another strategy made use of the natural diversity of ScFv libraries prepared with CDRs from the immunologically naive germline antibody genes (Griffiths et al., 1993; Marks et al., 1991). A third approach to generating diversity seeks to improve the affinity of selected antibodies by allowing random or directed reassortment of cloned VH and VL regions (Marks et al., 1992). This type of diversity has been called "chain shuffling." Another recently published method allows combinatorial shuffling of individual intact CDRs (Crameri and Stemmer, 1995).

Methods of Detecting Antibodies and Polypeptides

The present invention also provides methods of detecting a rhesus monkey BCRP polypeptide, comprising one or more of the following steps in any effective order, e.g., contacting a sample comprising a rhesus monkey BCRP polypeptide with an antibody specific for it under conditions effective for said antibody to specifically bind to said polypeptide; and detecting said specific binding of said antibody to said BCRP polypeptide. Specific binding of antibodies and other binding partners to BRCP polypeptides, or fragments thereof, can be detected, visualized, determined, quantitated, etc. according to any effective method. Useful methods include, e.g., but are not limited to, immunoassays, RIA (radioimmunassay), ELISA, (enzyme-linked-immunosorbent assay), immunofluorescence, flow cytometry (e.g., fluorescence activated cell sorting or FACS), histology, electron microscopy, light microscopy, in situ assays, immunoprecipitation, Western blot, etc. Antibodies can be detected similarly, e.g., where the purpose is to screen for antibodies that body to a BCRP target polypeptide of interest.

The assays are generally carried out under effective conditions. Such conditions include any environment in which the purpose of the assay can be accomplished, e.g., to permit specific binding between an antibody and antigen of interest. These include, suitable antibody and antigen concentrations; temperature; buffer; the presence of any agent that facilitates the interaction, including proteins and other additives to reduce non-specific binding; etc. Specific binding indicates the binding of a binding partner to a defined amino acid sequence (see above) in contrast to "non-specific binding" to other unintended sequences.

Assays can be carried in liquid or on biological support. For instance, a sample (e.g., blood, stool, urine, cells, stem cells, tissue, cerebral spinal fluid, body fluids, etc.) can be brought in contact with and immobilized onto a solid phase support or carrier such as nitrocellulose, or other solid support that is capable of immobilizing cells, cell particles or soluble proteins. The support may then be washed with suitable buffers followed by treatment with a detectably labeled specific antibody. The solid phase support can then be washed with a buffer a second time to remove unbound antibody. The amount of bound label on solid support may then be detected by conventional means.

A "solid phase support or carrier" includes any support capable of binding an antigen, antibody, or other specific binding partner. Supports or carriers include glass, polystyrene, polypropylene, polyethylene, dextran, nylon, amylases, natural and modified celluloses, polyacrylamides, and magnetite. A support material can have any structural or physical configuration. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads.

One of the many ways in which polypeptide-specific antibody can be detectably labeled is by linking it to an enzyme and using it in an enzyme immunoassay (EIA). See, e.g., Voller, A., "The Enzyme Linked Immunosorbent Assay (ELISA)," 1978, Diagnostic Horizons 2, 1-7, Microbiological Associates Quarterly Publication, Walkersville, Md.); Voller, A. et al., 1978, J. Clin. Pathol. 31, 507-520; Butler, J. E., 1981, Meth. Enzymol. 73, 482-523; Maggio, E. (ed.), 1980, Enzyme Immunoassay, CRC Press, Boca Raton, Fla. The enzyme which is bound to the antibody will react with an appropriate substrate, preferably a chromogenic substrate, in such a manner as to produce a chemical moiety that can be detected, for example, by spectrophotometric, fluorimetric or by visual means. Enzymes that can be used to detectably label the antibody include, but are not limited to, malate dehydrogenase, staphylococcal nuclease, delta-5-steroid isomerase, yeast alcohol dehydrogenase, alpha.-glycerophosphate, dehydrogenase, triose phosphate isomerase, horseradish peroxidase, alkaline phosphatase, asparaginase, glucose oxidase, .beta.-galactosidase, ribonuclease, urease, catalase, glucose-6-phosphate dehydrogenase, glucoamylase and acetylcholinesterase. The detection can be accomplished by colorimetric methods that employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect polypeptides through the use of a radioimmunoassay (RIA). See, e.g., Weintraub, B., Principles of Radioimmunoassays, Seventh Training Course on Radioligand Assay Techniques, The Endocrine Society, March, 1986. The radioactive isotope can be detected by such means as the use of a gamma counter or a scintillation counter or by autoradiography.

It is also possible to label the antibody with a fluorescent compound. When the fluorescently labeled antibody is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine. See above for others. The antibody can also be detectably labeled using fluorescence emitting metals such as those in the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The term "isolated" as used herein indicates that the product is present in a form which does not naturally occur in nature, e.g., separated, enriched, purified, and otherwise modified. The term "obtainable" as used herein indicates that product can be obtained from the identified source (e.g., monkey), but a product having identical characteristics can also be produced by other methods, e.g., by recombinant expression or genetic engineering.

The topic headings set forth above are meant as guidance where certain information can be found in the application, but are not intended to be the only source in the application where information on such topic can be found.

For other aspects of the polynucleotides, reference is made to standard textbooks of molecular biology. See, e.g., Hames et al., *Polynucleotide Hybridization*, IL Press, 1985; Davis et al., *Basic Methods in Molecular Biology*, Elsevier Sciences Publishing, Inc., New York, 1986; Sambrook et al., *Molecular Cloning*, CSH Press, 1989; Howe, *Gene Cloning and Manipulation*, Cambridge University Press, 1995; Ausubel et al., *Current Protocols in Molecular Biology*, John Wiley & Sons, Inc., 1994-1998.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. The entire disclosure of all applications, patents and publications, cited above and in the figures are hereby incorporated by reference in their entirety.

EXAMPLES

Cloning of Rhesus Macaque Breast Cancer Resistance Protein (BCRP)

Full-length sequence was obtained using two strategies. In both strategies, the source of total RNA from rhesus pancreas islet cells was employed. Total RNA was extracted using standard methods.

1. A fragment of rhesus BCRP was amplified by RT-PCR using a set of primers which was known to be able to detect rhesus BCRP (300 bp fragment) (see Sheng Zhou, John D. Shuetz, Kevin D. Bunting, et al. "The ABC transporter Bcrp1/

ABCG2 is expressed in a wide variety of stem cells and is a molecular determinant of the side-population phenotype. Nature Medicine 2001, vol. 7, 1028, incorporated herein by reference in its entirety). The amplified fragment was sequenced and used to design GSP 1 and GSP2 primers, which were used to perform RACE technology (GSP 1-1: 5'-gctgatctccttgaagactgtga-3' (SEQ ID NO:9): and GSP2-1: 5'-atactttgaatcagctggttatc-3' (SEQ ID NO:10).

SMART RACE cDNA amplification kit (Clontech) was used according to the manufacturer's instructions. In brief, we designed primers GSP1 and GSP2 for 5' RACE and 3' RACE, respectively, based on our 300 bp cDNA rhesus BCRP product sequences as described above. We synthesized cDNA to the both ends from this partial sequence using the RACE technology. After an each round of RACE, an elongated product was submitted for sequencing. Then, a new set of primer was designed each time based on a new sequence for the further cDNA extension. After 3 rounds of RACE, the full length cDNA sequence for rhesus BCRP (SEQ ID NO:1) was determined.

2. The rhesus BCRP cDNA was cloned by RT-PCR using two primers (Rhesus BCRP forward: 5'-aaagataaaaactctcca-gatgtc-3' (SEQ ID NO:11); and Rhesus BCRP reverse: 5'-ttaagaatattttttaagaaataacaat-3', (SEQ ID NO:12), which were designed based on our cDNA sequence generated in (1). The same RNA was used as described herein.

What I claim:

1. An isolated polypeptide which is
   a) a polypeptide comprising an amino acid sequence of SEQ ID NO:2, or
   b) a polypeptide which is encoded by a polynucleotide sequence comprising SEQ ID NO: 1.

2. An isolated polypeptide comprising a polypeptide which is encoded by a polynucleotide sequence, wherein said polynucleotide sequence hybridizes over the full length of the complement of SEQ ID NO: 1 under conditions comprising overnight incubation at 42° C in a solution comprising 5x SSC, 0.5% SDS, 100 µg/ml denatured salmon sperm DNA and 50% formamide; followed by washing at 65° C in 0.1% SSC and 0.1% SDS.

3. An isolated polypeptide of claim 2 which comprises at least one rhesus monkey isoform-specific residue which is T242, P340, K357, G411, or T615 of SEQ ID NO:2.

4. An isolated polypeptide of claim 2, which comprises at least one rhesus monkey-specific residue which is M12, T22, R28, V48, G55, P149, V329, D338, I404, G411, N417, F471, T502, I508, V599, or T602 of SEQ ID NO:2

5. An isolated polypeptide of claim 2 wherein said polypeptide has at least one amino acid substitution at amino acid positions 242, 340, 357, 411, and/or 615 of SEQ ID NO:2, other than the amino acid which occurs in SEQ ID NO: 2, SEQ ID NO: 5, SEQ ID NO: 6, SEQ ID NO: 7 or SEQ ID NO: 8.

6. An isolated polypeptide of claim 2 wherein said polypeptide has at least one amino acid substitution at amino acid positions 12, 22, 28, 48, 55, 149, 329, 338, 404, 411, 417, 471, 502, 508, 599, and 602 of SEQ ID NO:2, other than the amino acid which occurs in SEQ ID NO: 2, SEQ ID NO: 5, SEQ ID NO: 6, SEQ ID NO:7 or SEQ ID NO: 8.

7. An isolated polypeptide of claim 2, which is obtainable from rhesus monkey and which comprises T615 of SEQ ID NO:2.

8. An isolated polypeptide of claim 1, which consists of the amino acid sequence set forth in SEQ ID NO:2.

9. An isolated polypeptide which consists of the amino acid sequence set forth in SEQ ID NO:4.

10. An isolated polypeptide of claim 9, which consists of a polypeptide which is encoded by a polynucleotide sequence which hybridizes over the full length of the complement of SEQ ID NO:3 under high stringency conditions, wherein high stringency conditions comprise overnight incubation at 42° C in a solution comprising 5x SSC, 0.5% SDS, 100 μg/ml denatured salmon sperm DNA and 50% formamide, followed by washing at 65° C in 0.1% SSC and 0.1% SDS.

11. An isolated polypeptide of claim 10, wherein said polypeptide comprises T615 of SEQ ID NO:2.

* * * * *

SEQUENCE LISTING

<160> NUMBER OF SEQ ID NOS: 13

<210> SEQ ID NO 1
<211> LENGTH: 2285
<212> TYPE: DNA
<213> ORGANISM: Macaca mulatta

<400> SEQUENCE: 1

```
gagctcatta gcggaaagat aaaaactctc cagatgtctt ccagtaatgt cgaagttttt      60
atcccaatgt cacaagaaaa caccaatggc ttccccacga caacttccaa tgaccggaag     120
gcatttactg aaggagctgt gttaagtttt cataacatct gctatcgagt aaaagtgaag     180
agtggctttc tacctggtcg aaaaccagtt gagaaagaaa tactatcgaa tatcaatggg     240
atcatgaaac ctggcctcaa tgccattctg ggacccacag gtggaggcaa atcttcgtta     300
ttagatgtct tagctgcaag gaaagatcca agtggattgt ctggagatgt tctgataaat     360
ggagcactgc gacctaccaa tttcaaatgt aattcaggtt acgtggtaca agatgatgtc     420
gtgatgggca ctctgacggt gagagaaaac ttacagttct cagcagctct tcggcttcca     480
acaactatga cgaatcatga aaaaacgaa cggattaaca gggtcattca agagtttgggt     540 ctggataaag tggcagactc caaggttgga actcaattta tccgtggtgt gtccggagga     600
gaaagaaaaa ggactagtat aggaatggag cttatcactg atccttccat cttgttcttg     660
gacgagccta acacaggctt agactcaagc acagcaaatg ctgtcctttt gctcctgaaa     720
aggatgtcta agcagggacg aacaatcatc ttctccactc atcagcctcg atattccatc     780
ttcaagttgt ttgatagtct caccttattg gcctcaggaa gacttatgtt ccatggacct     840
gctcaggagg ccttgggata ctttgaatca gctggttatc actgtgaggc ctataataac     900
cctgcggact tcttcttgga catcattaat ggagattcca ctgctgtggc attaaacaga     960
gaagaagact ttaaagccac ggagatcata gagccttcca agcgggataa gccactcgta    1020
gaaaaattag ccgagattta tgtcgactcc cccttctaca aagagacaaa agctgaatta    1080
catcaacttt ccggggtga agaagaag aagatcacag tcttcaagga gatcagctac    1140
accacctcct tctgtcatca actcagatgg gtttccaagc gttcattcaa aaacttgctg    1200
ggtaatcccc aggcctctat agctcagatc attgtcacag tcatactggg actggttata    1260
ggtggcattt actttgggct aaacaatgat tctactggaa tccagaacag agccggggtt    1320
ctcttctttc tgacgaccaa ccagtgtttc agcagcgtgt cggccgtgga actctttgtg    1380
gtagagaaga gctcttcat acatgaatac atcagcggat actacagagt gtcatcttat    1440 tttttggaa aactgttatc tgatttatta cccatgagga tgttaccaag tattatattt    1500
```

-continued

```
acctgtatag tgtacttcat gttaggattg aagccaacgg cagacgcctt cttcattatg    1560
atgtttaccc ttatgatggt ggcttattcg gccagttcca tggcactggc catagcagca    1620
ggtcagagtg tggtttccgt agcaacactt ctcatgacca tctgttttgt gtttatgatg    1680
attttttcgg gtctgttggt caatctcaca accattgcat cttggctgtc atggcttcag    1740
tacttcagca ttccacgata tggatttacg gctttgcagc ataatgaatt tttgggacaa    1800
aacttctgcc caggactcaa tgcaacagta acaatacttt gtaactatgc aacatgtact    1860
ggtgaagaat atttgacaaa gcagggcatc gatctctcac cctggggctt gtggaagaat    1920
cacgtggcct tggcttgtat gattgttatt ttcctcacaa ttgcctacct gaaattgtta    1980
tttcttaaaa aatattctta aatttcccct taattcagta tgatttatcc tcacataaga    2040
aagaagcacc ttgattgaag tattcaatca agttttttg ttgttttctg ttcccttgct     2100
gtcacactgt tgcgcaatag cagttgtttt aaagagatac attttagaa atcacaacaa     2160 atggaattaa acatgaaaga tccaagata tcatgtatcg catattagtt catctcctca     2220
gacagtaacc atgggcaaga aatctagtct aacttattaa cctaaaaagg gagaattgaa    2280
ttctg                                                                2285
```

<210> SEQ ID NO 2
<211> LENGTH: 655
<212> TYPE: PRT
<213> ORGANISM: Macaca mulatta

<400> SEQUENCE: 2

```
Met Ser Ser Ser Asn Val Glu Val Phe Ile Pro Met Ser Gln Glu Asn
  1               5                  10                  15

Thr Asn Gly Phe Pro Thr Thr Thr Ser Asn Asp Arg Lys Ala Phe Thr
             20                  25                  30

Glu Gly Ala Val Leu Ser Phe His Asn Ile Cys Tyr Arg Val Lys Val
         35                  40                  45

Lys Ser Gly Phe Leu Pro Gly Arg Lys Pro Val Glu Lys Glu Ile Leu
     50                  55                  60

Ser Asn Ile Asn Gly Ile Met Lys Pro Gly Leu Asn Ala Ile Leu Gly
 65                  70                  75                  80

Pro Thr Gly Gly Lys Ser Ser Leu Leu Asp Val Leu Ala Ala Arg
                 85                  90                  95

Lys Asp Pro Ser Gly Leu Ser Gly Asp Val Leu Ile Asn Gly Ala Leu
            100                 105                 110

Arg Pro Thr Asn Phe Lys Cys Asn Ser Gly Tyr Val Val Gln Asp Asp
        115                 120                 125

Val Val Met Gly Thr Leu Thr Val Arg Glu Asn Leu Gln Phe Ser Ala
    130                 135                 140

Ala Leu Arg Leu Pro Thr Thr Met Thr Asn His Glu Lys Asn Glu Arg
145                 150                 155                 160

Ile Asn Arg Val Ile Gln Glu Leu Gly Leu Asp Lys Val Ala Asp Ser
                165                 170                 175

Lys Val Gly Thr Gln Phe Ile Arg Gly Val Ser Gly Gly Glu Arg Lys
            180                 185                 190

Arg Thr Ser Ile Gly Met Glu Leu Ile Thr Asp Pro Ser Ile Leu Phe
        195                 200                 205

Leu Asp Glu Pro Thr Thr Gly Leu Asp Ser Ser Thr Ala Asn Ala Val
    210                 215                 220
```

-continued

```
Leu Leu Leu Leu Lys Arg Met Ser Lys Gln Gly Arg Thr Ile Ile Phe
225                 230                 235                 240

Ser Thr His Gln Pro Arg Tyr Ser Ile Phe Lys Leu Phe Asp Ser Leu
            245                 250                 255

Thr Leu Leu Ala Ser Gly Arg Leu Met Phe His Gly Pro Ala Gln Glu
        260                 265                 270

Ala Leu Gly Tyr Phe Glu Ser Ala Gly Tyr His Cys Glu Ala Tyr Asn
    275                 280                 285

Asn Pro Ala Asp Phe Phe Leu Asp Ile Ile Asn Gly Asp Ser Thr Ala
290                 295                 300

Val Ala Leu Asn Arg Glu Glu Asp Phe Lys Ala Thr Glu Ile Ile Glu
305                 310                 315                 320

Pro Ser Lys Arg Asp Lys Pro Leu Val Glu Lys Leu Ala Glu Ile Tyr
            325                 330                 335

Val Asp Ser Pro Phe Tyr Lys Glu Thr Lys Ala Glu Leu His Gln Leu
        340                 345                 350

Ser Gly Gly Glu Lys Lys Lys Ile Thr Val Phe Lys Glu Ile Ser
    355                 360                 365

Tyr Thr Thr Ser Phe Cys His Gln Leu Arg Trp Val Ser Lys Arg Ser
370                 375                 380

Phe Lys Asn Leu Leu Gly Asn Pro Gln Ala Ser Ile Ala Gln Ile Ile
385                 390                 395                 400

Val Thr Val Ile Leu Gly Leu Val Ile Gly Gly Ile Tyr Phe Gly Leu
            405                 410                 415

Asn Asn Asp Ser Thr Gly Ile Gln Asn Arg Ala Gly Val Leu Phe Phe
        420                 425                 430

Leu Thr Thr Asn Gln Cys Phe Ser Ser Val Ser Ala Val Glu Leu Phe
    435                 440                 445

Val Val Glu Lys Lys Leu Phe Ile His Glu Tyr Ile Ser Gly Tyr Tyr
450                 455                 460

Arg Val Ser Ser Tyr Phe Phe Gly Lys Leu Leu Ser Asp Leu Leu Pro
465                 470                 475                 480

Met Arg Met Leu Pro Ser Ile Ile Phe Thr Cys Ile Val Tyr Phe Met
            485                 490                 495

Leu Gly Leu Lys Pro Thr Ala Asp Ala Phe Phe Ile Met Met Phe Thr
        500                 505                 510

Leu Met Met Val Ala Tyr Ser Ala Ser Ser Met Ala Leu Ala Ile Ala
    515                 520                 525

Ala Gly Gln Ser Val Val Ser Val Ala Thr Leu Leu Met Thr Ile Cys
530                 535                 540

Phe Val Phe Met Met Ile Phe Ser Gly Leu Leu Val Asn Leu Thr Thr
545                 550                 555                 560

Ile Ala Ser Trp Leu Ser Trp Leu Gln Tyr Phe Ser Ile Pro Arg Tyr
            565                 570                 575

Gly Phe Thr Ala Leu Gln His Asn Glu Phe Leu Gly Gln Asn Phe Cys
        580                 585                 590

Pro Gly Leu Asn Ala Thr Val Asn Asn Thr Cys Asn Tyr Ala Thr Cys
    595                 600                 605

Thr Gly Glu Glu Tyr Leu Thr Lys Gln Gly Ile Asp Leu Ser Pro Trp
610                 615                 620

Gly Leu Trp Lys Asn His Val Ala Leu Ala Cys Met Ile Val Ile Phe
625                 630                 635                 640

Leu Thr Ile Ala Tyr Leu Lys Leu Leu Phe Leu Lys Lys Tyr Ser
```

```
                        645                 650                 655

<210> SEQ ID NO 3
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aactatgcaa catgtactgg tgaagaatat ttgacaaagc agggcatcga tctctca          57

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asn Tyr Ala Thr Cys Thr Gly Glu Glu Tyr Leu Thr Lys Gln Gly Ile
  1               5                  10                  15

Asp Leu Ser

<210> SEQ ID NO 5
<211> LENGTH: 654
<212> TYPE: PRT
<213> ORGANISM: Macaca mulatta

<400> SEQUENCE: 5

Met Ser Ser Ser Asn Val Glu Val Phe Ile Pro Met Ser Gln Glu Asn
  1               5                  10                  15

Thr Asn Gly Phe Pro Thr Thr Thr Ser Asn Asp Arg Lys Ala Phe Thr
                 20                  25                  30

Glu Gly Ala Val Leu Ser Phe His Asn Ile Cys Tyr Arg Val Lys Val
             35                  40                  45

Lys Ser Gly Phe Leu Pro Gly Arg Lys Pro Val Glu Lys Glu Ile Leu
         50                  55                  60

Ser Asn Ile Asn Gly Ile Met Lys Pro Gly Leu Asn Ala Ile Leu Gly
 65                  70                  75                  80

Pro Thr Gly Gly Gly Lys Ser Ser Leu Leu Asp Val Leu Ala Ala Arg
                 85                  90                  95

Lys Asp Pro Ser Gly Leu Ser Gly Asp Val Leu Ile Asn Gly Ala Leu
            100                 105                 110

Arg Pro Thr Asn Phe Lys Cys Asn Ser Gly Tyr Val Val Gln Asp Asp
            115                 120                 125

Val Val Met Gly Thr Leu Thr Val Arg Glu Asn Leu Gln Phe Ser Ala
        130                 135                 140

Ala Leu Arg Leu Pro Thr Thr Met Thr Asn His Glu Lys Asn Glu Arg
145                 150                 155                 160

Ile Asn Arg Val Ile Gln Glu Leu Gly Leu Asp Lys Val Ala Asp Ser
                165                 170                 175

Lys Val Gly Thr Gln Phe Ile Arg Gly Val Ser Gly Gly Glu Arg Lys
            180                 185                 190

Arg Thr Ser Ile Gly Met Glu Leu Ile Thr Asp Pro Ser Ile Leu Phe
            195                 200                 205

Leu Asp Glu Pro Thr Thr Gly Leu Asp Ser Ser Thr Ala Asn Ala Val
```

-continued

```
            210                 215                 220
Leu Leu Leu Leu Lys Arg Met Ser Lys Gln Gly Arg Thr Ile Ile Phe
225                 230                 235                 240

Ser Ile His Gln Pro Arg Tyr Ser Ile Phe Lys Leu Phe Asp Ser Leu
                245                 250                 255

Thr Leu Leu Ala Ser Gly Arg Leu Met Phe His Gly Pro Ala Gln Glu
            260                 265                 270

Ala Leu Gly Tyr Phe Glu Ser Ala Gly Tyr His Cys Glu Ala Tyr Asn
                275                 280                 285

Asn Pro Ala Asp Phe Phe Leu Asp Ile Ile Asn Gly Asp Ser Thr Ala
290                 295                 300

Val Ala Leu Asn Arg Glu Glu Asp Phe Lys Ala Thr Glu Ile Ile Glu
305                 310                 315                 320

Pro Ser Lys Arg Asp Lys Pro Leu Val Glu Lys Leu Ala Glu Ile Tyr
                325                 330                 335

Val Asp Ser Ser Phe Tyr Lys Glu Thr Lys Ala Glu Leu His Gln Leu
                340                 345                 350

Ser Gly Gly Glu Lys Lys Lys Ile Thr Val Phe Lys Glu Ile Ser Tyr
            355                 360                 365

Thr Thr Ser Phe Cys His Gln Leu Arg Trp Val Ser Lys Arg Ser Phe
            370                 375                 380

Lys Asn Leu Leu Gly Asn Pro Gln Ala Ser Ile Ala Gln Ile Ile Val
385                 390                 395                 400

Thr Val Ile Leu Gly Leu Val Ile Gly Ala Ile Tyr Phe Gly Leu Asn
                405                 410                 415

Asn Asp Ser Thr Gly Ile Gln Asn Arg Ala Gly Val Leu Phe Phe Leu
            420                 425                 430

Thr Thr Asn Gln Cys Phe Ser Ser Val Ser Ala Val Glu Leu Phe Val
            435                 440                 445

Val Glu Lys Lys Leu Phe Ile His Glu Tyr Ile Ser Gly Tyr Tyr Arg
    450                 455                 460

Val Ser Ser Tyr Phe Phe Gly Lys Leu Leu Ser Asp Leu Leu Pro Met
465                 470                 475                 480

Arg Met Leu Pro Ser Ile Ile Phe Thr Cys Ile Val Tyr Phe Met Leu
                485                 490                 495

Gly Leu Lys Pro Thr Ala Asp Ala Phe Phe Ile Met Met Phe Thr Leu
                500                 505                 510

Met Met Val Ala Tyr Ser Ala Ser Ser Met Ala Leu Ala Ile Ala Ala
            515                 520                 525

Gly Gln Ser Val Val Ser Val Ala Thr Leu Leu Met Thr Ile Cys Phe
        530                 535                 540

Val Phe Met Met Ile Phe Ser Gly Leu Leu Val Asn Leu Thr Thr Ile
545                 550                 555                 560

Ala Ser Trp Leu Ser Trp Leu Gln Tyr Phe Ser Ile Pro Arg Tyr Gly
                565                 570                 575

Phe Thr Ala Leu Gln His Asn Glu Phe Leu Gly Gln Asn Phe Cys Pro
            580                 585                 590

Gly Leu Asn Ala Thr Val Asn Asn Thr Cys Asn Tyr Ala Thr Cys Thr
            595                 600                 605

Gly Glu Glu Tyr Leu Ala Lys Gln Gly Ile Asp Leu Ser Pro Trp Gly
    610                 615                 620

Leu Trp Lys Asn His Val Ala Leu Ala Cys Met Ile Val Ile Phe Leu
625                 630                 635                 640
```

```
Thr Ile Ala Tyr Leu Lys Leu Leu Phe Leu Lys Lys Tyr Ser
            645                 650
```

<210> SEQ ID NO 6
<211> LENGTH: 655
<212> TYPE: PRT
<213> ORGANISM: Homo sapiens

<400> SEQUENCE: 6

```
Met Ser Ser Asn Val Glu Val Phe Ile Pro Val Ser Gln Gly Asn
  1               5                  10                  15

Thr Asn Gly Phe Pro Ala Thr Ala Ser Asn Asp Leu Lys Ala Phe Thr
                 20                  25                  30

Glu Gly Ala Val Leu Ser Phe His Asn Ile Cys Tyr Arg Val Lys Leu
             35                  40                  45

Lys Ser Gly Phe Leu Pro Cys Arg Lys Pro Val Glu Lys Glu Ile Leu
     50                  55                  60

Ser Asn Ile Asn Gly Ile Met Lys Pro Gly Leu Asn Ala Ile Leu Gly
 65                  70                  75                  80

Pro Thr Gly Gly Lys Ser Ser Leu Leu Asp Val Leu Ala Ala Arg
                 85                  90                  95

Lys Asp Pro Ser Gly Leu Ser Gly Asp Val Leu Ile Asn Gly Ala Pro
            100                 105                 110

Arg Pro Ala Asn Phe Lys Cys Asn Ser Gly Tyr Val Gln Asp Asp
            115                 120                 125

Val Val Met Gly Thr Leu Thr Val Arg Glu Asn Leu Gln Phe Ser Ala
        130                 135                 140

Ala Leu Arg Leu Ala Thr Thr Met Thr Asn His Glu Lys Asn Glu Arg
145                 150                 155                 160

Ile Asn Arg Val Ile Gln Glu Leu Gly Leu Asp Lys Val Ala Asp Ser
                165                 170                 175

Lys Val Gly Thr Gln Phe Ile Arg Gly Val Ser Gly Gly Glu Arg Lys
            180                 185                 190

Arg Thr Ser Ile Gly Met Glu Leu Ile Thr Asp Pro Ser Ile Leu Phe
        195                 200                 205

Leu Asp Glu Pro Thr Thr Gly Leu Asp Ser Ser Thr Ala Asn Ala Val
210                 215                 220

Leu Leu Leu Leu Lys Arg Met Ser Lys Gln Gly Arg Thr Ile Ile Phe
225                 230                 235                 240

Ser Ile His Gln Pro Arg Tyr Ser Ile Phe Lys Leu Phe Asp Ser Leu
                245                 250                 255

Thr Leu Leu Ala Ser Gly Arg Leu Met Phe His Gly Pro Ala Gln Glu
            260                 265                 270

Ala Leu Gly Tyr Phe Glu Ser Ala Gly Tyr His Cys Glu Ala Tyr Asn
        275                 280                 285

Asn Pro Ala Asp Phe Phe Leu Asp Ile Ile Asn Gly Asp Ser Thr Ala
    290                 295                 300

Val Ala Leu Asn Arg Glu Asp Phe Lys Ala Thr Glu Ile Ile Glu
305                 310                 315                 320

Pro Ser Lys Gln Asp Lys Pro Leu Ile Glu Lys Leu Ala Glu Ile Tyr
                325                 330                 335

Val Asn Ser Ser Phe Tyr Lys Glu Thr Lys Ala Glu Leu His Gln Leu
            340                 345                 350

Ser Gly Gly Glu Lys Lys Lys Lys Ile Thr Val Phe Lys Glu Ile Ser
```

```
                355                 360                 365
Tyr Thr Thr Ser Phe Cys His Gln Leu Arg Trp Val Ser Lys Arg Ser
    370                 375                 380

Phe Lys Asn Leu Leu Gly Asn Pro Gln Ala Ser Ile Ala Gln Ile Ile
385                 390                 395                 400

Val Thr Val Val Leu Gly Leu Val Ile Gly Ala Ile Tyr Phe Gly Leu
                405                 410                 415

Lys Asn Asp Ser Thr Gly Ile Gln Asn Arg Ala Gly Val Leu Phe Phe
            420                 425                 430

Leu Thr Thr Asn Gln Cys Phe Ser Ser Val Ser Ala Val Glu Leu Phe
        435                 440                 445

Val Val Glu Lys Lys Leu Phe Ile His Glu Tyr Ile Ser Gly Tyr Tyr
    450                 455                 460

Arg Val Ser Ser Tyr Phe Leu Gly Lys Leu Leu Ser Asp Leu Leu Pro
465                 470                 475                 480

Met Arg Met Leu Pro Ser Ile Ile Phe Thr Cys Ile Val Tyr Phe Met
                485                 490                 495

Leu Gly Leu Lys Pro Lys Ala Asp Ala Phe Phe Val Met Met Phe Thr
            500                 505                 510

Leu Met Met Val Ala Tyr Ser Ala Ser Ser Met Ala Leu Ala Ile Ala
        515                 520                 525

Ala Gly Gln Ser Val Val Ser Val Ala Thr Leu Leu Met Thr Ile Cys
    530                 535                 540

Phe Val Phe Met Met Ile Phe Ser Gly Leu Leu Val Asn Leu Thr Thr
545                 550                 555                 560

Ile Ala Ser Trp Leu Ser Trp Leu Gln Tyr Phe Ser Ile Pro Arg Tyr
                565                 570                 575

Gly Phe Thr Ala Leu Gln His Asn Glu Phe Leu Gly Gln Asn Phe Cys
            580                 585                 590

Pro Gly Leu Asn Ala Thr Gly Asn Pro Cys Asn Tyr Ala Thr Cys
        595                 600                 605

Thr Gly Glu Glu Tyr Leu Val Lys Gln Gly Ile Asp Leu Ser Pro Trp
    610                 615                 620

Gly Leu Trp Lys Asn His Val Ala Leu Ala Cys Met Ile Val Ile Phe
625                 630                 635                 640

Leu Thr Ile Ala Tyr Leu Lys Leu Leu Phe Leu Lys Lys Tyr Ser
                645                 650                 655

<210> SEQ ID NO 7
<211> LENGTH: 655
<212> TYPE: PRT
<213> ORGANISM: Homo sapiens

<400> SEQUENCE: 7

Met Ser Ser Ser Asn Val Glu Val Phe Ile Pro Val Ser Gln Gly Asn
  1               5                  10                  15

Thr Asn Gly Phe Pro Ala Thr Val Ser Asn Asp Leu Lys Ala Phe Thr
             20                  25                  30

Glu Gly Ala Val Leu Ser Phe His Asn Ile Cys Tyr Arg Val Lys Leu
         35                  40                  45

Lys Ser Gly Phe Leu Pro Cys Arg Lys Pro Val Glu Lys Glu Ile Leu
     50                  55                  60

Ser Asn Ile Asn Gly Ile Met Lys Pro Gly Leu Asn Ala Ile Leu Gly
 65                  70                  75                  80
```

-continued

```
Pro Thr Gly Gly Gly Lys Ser Ser Leu Leu Asp Val Leu Ala Ala Arg
                85                  90                  95

Lys Asp Pro Ser Gly Leu Ser Gly Asp Val Leu Ile Asn Gly Ala Pro
            100                 105                 110

Arg Pro Ala Asn Phe Lys Cys Asn Ser Gly Tyr Val Val Gln Asp Asp
            115                 120                 125

Val Val Met Gly Thr Leu Thr Val Arg Glu Asn Leu Gln Phe Ser Ala
        130                 135                 140

Ala Leu Arg Leu Ala Thr Thr Met Thr Asn His Glu Lys Asn Glu Arg
145                 150                 155                 160

Ile Asn Arg Val Ile Glu Glu Leu Gly Leu Asp Lys Val Ala Asp Ser
                165                 170                 175

Lys Val Gly Thr Gln Phe Ile Arg Gly Val Ser Gly Gly Glu Arg Lys
            180                 185                 190

Arg Thr Ser Ile Gly Met Glu Leu Ile Thr Asp Pro Ser Ile Leu Ser
        195                 200                 205

Leu Asp Glu Pro Thr Thr Gly Leu Asp Ser Ser Thr Ala Asn Ala Val
210                 215                 220

Leu Leu Leu Leu Lys Arg Met Ser Lys Gln Gly Arg Thr Ile Ile Phe
225                 230                 235                 240

Ser Ile His Gln Pro Arg Tyr Ser Ile Phe Lys Leu Phe Asp Ser Leu
                245                 250                 255

Thr Leu Leu Ala Ser Gly Arg Leu Met Phe His Gly Pro Ala Gln Glu
            260                 265                 270

Ala Leu Gly Tyr Phe Glu Ser Ala Gly Tyr His Cys Glu Ala Tyr Asn
        275                 280                 285

Asn Pro Ala Asp Phe Phe Leu Asp Ile Ile Asn Gly Asp Ser Thr Ala
        290                 295                 300

Val Ala Leu Asn Arg Glu Glu Asp Phe Lys Ala Thr Glu Ile Ile Glu
305                 310                 315                 320

Pro Ser Lys Gln Asp Lys Pro Leu Ile Glu Lys Leu Ala Glu Ile Tyr
                325                 330                 335

Val Asn Ser Ser Phe Tyr Lys Glu Thr Lys Ala Glu Leu His Gln Leu
            340                 345                 350

Ser Gly Gly Glu Lys Lys Lys Lys Ile Thr Val Phe Lys Glu Ile Ser
        355                 360                 365

Tyr Thr Thr Ser Phe Cys His Gln Leu Arg Trp Val Ser Lys Arg Ser
        370                 375                 380

Phe Lys Asn Leu Leu Gly Asn Pro Gln Ala Ser Ile Ala Gln Ile Ile
385                 390                 395                 400

Val Thr Val Val Leu Gly Leu Val Ile Gly Ala Ile Tyr Phe Gly Leu
                405                 410                 415

Lys Asn Asp Ser Thr Gly Ile Gln Asn Arg Ala Gly Val Leu Phe Phe
            420                 425                 430

Leu Thr Thr Asn Gln Cys Phe Ser Ser Val Ser Ala Val Glu Leu Phe
        435                 440                 445

Val Val Glu Lys Lys Leu Phe Ile His Glu Tyr Ile Ser Gly Tyr Tyr
        450                 455                 460

Arg Val Ser Ser Tyr Phe Leu Gly Lys Leu Leu Ser Asp Leu Leu Pro
465                 470                 475                 480

Met Arg Met Leu Pro Ser Ile Ile Phe Thr Cys Ile Val Tyr Phe Met
                485                 490                 495

Leu Gly Leu Lys Pro Lys Ala Asp Ala Phe Phe Val Met Met Phe Thr
```

```
                500             505             510
Leu Met Met Val Ala Tyr Ser Ala Ser Met Ala Leu Ala Ile Ala
            515                 520             525

Ala Gly Gln Ser Val Val Ser Val Ala Thr Leu Leu Met Thr Ile Cys
    530                 535                 540

Phe Val Phe Met Met Ile Phe Ser Gly Leu Leu Val Asn Leu Thr Thr
545                 550                 555                 560

Ile Ala Ser Trp Leu Ser Trp Leu Gln Tyr Phe Ser Ile Pro Arg Tyr
                565                 570                 575

Gly Phe Thr Ala Leu Gln His Asn Glu Phe Leu Gly Gln Asn Phe Cys
            580                 585                 590

Pro Gly Leu Asn Ala Thr Gly Asn Asn Pro Cys Asn Tyr Ala Thr Cys
        595                 600                 605

Thr Gly Glu Glu Tyr Leu Val Lys Gln Gly Ile Asp Leu Ser Pro Trp
    610                 615                 620

Gly Leu Trp Lys Asn His Val Ala Leu Ala Cys Met Ile Val Ile Phe
625                 630                 635                 640

Leu Thr Ile Ala Tyr Leu Lys Leu Leu Phe Leu Lys Lys Tyr Ser
                645                 650                 655

<210> SEQ ID NO 8
<211> LENGTH: 655
<212> TYPE: PRT
<213> ORGANISM: Homo sapiens

<400> SEQUENCE: 8

Met Ser Ser Ser Asn Val Glu Val Phe Ile Pro Val Ser Gln Gly Asn
 1               5                  10                  15

Thr Asn Gly Phe Pro Ala Thr Ala Ser Asn Asp Leu Lys Ala Phe Thr
                20                  25                  30

Glu Gly Ala Val Leu Ser Phe His Asn Ile Cys Tyr Arg Val Lys Leu
            35                  40                  45

Lys Ser Gly Phe Leu Pro Cys Arg Lys Pro Val Glu Lys Glu Ile Leu
        50                  55                  60

Ser Asn Ile Asn Gly Ile Met Lys Pro Gly Leu Asn Ala Ile Leu Gly
65                  70                  75                  80

Pro Thr Gly Gly Gly Lys Ser Ser Leu Leu Asp Val Leu Ala Ala Arg
                85                  90                  95

Lys Asp Pro Ser Gly Leu Ser Gly Asp Val Leu Ile Asn Gly Ala Pro
            100                 105                 110

Arg Pro Ala Asn Phe Lys Cys Asn Ser Gly Tyr Val Val Gln Asp Asp
        115                 120                 125

Val Val Met Gly Thr Leu Thr Val Arg Glu Asn Leu Lys Phe Ser Ala
    130                 135                 140

Ala Leu Arg Leu Ala Thr Thr Met Thr Asn His Glu Lys Asn Glu Arg
145                 150                 155                 160

Ile Asn Arg Val Ile Gln Glu Leu Gly Leu Asp Lys Val Ala Asp Ser
                165                 170                 175

Lys Val Gly Thr Gln Phe Ile Arg Gly Val Ser Gly Gly Glu Arg Lys
            180                 185                 190

Arg Thr Ser Ile Gly Met Glu Leu Ile Thr Asp Pro Ser Ile Leu Phe
        195                 200                 205

Leu Asp Glu Pro Thr Thr Gly Leu Asp Ser Ser Thr Ala Asn Ala Val
    210                 215                 220
```

-continued

```
Leu Leu Leu Leu Lys Arg Met Ser Lys Gln Gly Arg Thr Ile Ile Phe
225                 230                 235                 240

Ser Ile His Gln Pro Arg Tyr Ser Ile Phe Lys Leu Phe Asp Ser Leu
                245                 250                 255

Thr Leu Leu Ala Ser Gly Arg Leu Met Phe His Gly Pro Ala Gln Glu
            260                 265                 270

Ala Leu Gly Tyr Phe Glu Ser Ala Gly Tyr His Cys Glu Ala Tyr Asn
        275                 280                 285

Asn Pro Ala Asp Phe Phe Leu Asp Ile Ile Asn Gly Asp Ser Thr Ala
    290                 295                 300

Val Ala Leu Asn Arg Glu Glu Asp Phe Lys Ala Thr Glu Ile Ile Glu
305                 310                 315                 320

Pro Ser Lys Gln Asp Lys Pro Leu Ile Glu Lys Leu Ala Glu Ile Tyr
                325                 330                 335

Val Asn Ser Ser Phe Tyr Lys Glu Thr Lys Ala Glu Leu His Gln Leu
            340                 345                 350

Ser Gly Gly Glu Lys Lys Lys Ile Thr Val Phe Lys Glu Ile Ser
        355                 360                 365

Tyr Thr Thr Ser Phe Cys His Gln Leu Arg Trp Val Ser Lys Arg Ser
    370                 375                 380

Phe Lys Asn Leu Leu Gly Asn Pro Gln Ala Ser Ile Ala Gln Ile Ile
385                 390                 395                 400

Val Thr Val Val Leu Gly Leu Val Ile Gly Ala Ile Tyr Phe Gly Leu
                405                 410                 415

Lys Asn Asp Ser Thr Gly Ile Gln Asn Arg Ala Gly Val Leu Phe Phe
            420                 425                 430

Leu Thr Thr Asn Gln Cys Phe Ser Ser Val Ser Ala Val Glu Leu Phe
        435                 440                 445

Val Val Glu Lys Lys Leu Phe Ile His Glu Tyr Ile Ser Gly Tyr Tyr
    450                 455                 460

Arg Val Ser Ser Tyr Phe Leu Gly Lys Leu Leu Ser Asp Leu Leu Pro
465                 470                 475                 480

Met Arg Met Leu Pro Ser Ile Ile Phe Thr Cys Ile Val Tyr Phe Met
                485                 490                 495

Leu Gly Leu Lys Pro Lys Ala Asp Ala Phe Phe Val Met Met Phe Thr
            500                 505                 510

Leu Met Met Val Ala Tyr Ser Ala Ser Ser Met Ala Leu Ala Ile Ala
        515                 520                 525

Ala Gly Gln Ser Val Val Ser Val Ala Thr Leu Leu Met Thr Ile Cys
    530                 535                 540

Phe Val Phe Met Met Ile Phe Ser Gly Leu Leu Val Asn Leu Thr Thr
545                 550                 555                 560

Ile Ala Ser Trp Leu Ser Trp Leu Gln Tyr Phe Ser Ile Pro Arg Tyr
                565                 570                 575

Gly Phe Thr Ala Leu Gln His Asn Glu Phe Leu Gly Gln Asn Phe Cys
            580                 585                 590

Pro Gly Leu Asn Ala Thr Gly Asn Asn Pro Cys Asn Tyr Ala Thr Cys
        595                 600                 605

Thr Gly Glu Glu Tyr Leu Val Lys Gln Gly Ile Asp Leu Ser Pro Trp
    610                 615                 620

Gly Leu Trp Lys Asn His Val Ala Leu Ala Cys Met Ile Val Ile Phe
625                 630                 635                 640
```

```
Leu Thr Ile Ala Tyr Leu Lys Leu Leu Phe Leu Lys Lys Tyr Ser
            645                 650                 655

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gctgatctcc ttgaagactg tga                                          23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
atactttgaa tcagctggtt atc                                          23

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aaagataaaa actctccaga tgtc                                         24

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttaagaatat tttttaagaa ataacaat                                     28

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 13

His His His His His His
 1               5
```